United States Patent [19]

Hayes

[11] Patent Number: 4,807,600
[45] Date of Patent: Feb. 28, 1989

[54] SPECULUM PROTECTOR

[76] Inventor: Allen L. Hayes, 7362 Creekview, West Bloomfield, Mich. 48033

[21] Appl. No.: 919,031

[22] Filed: Oct. 15, 1986

[51] Int. Cl.⁴ ............................................. A61B 1/32
[52] U.S. Cl. ...................................................... 128/17
[58] Field of Search ...................... 128/303.11, 303.12, 128/341, 345, 3, 7, 12, 17, 18, 20, 132 R, 11

[56] References Cited

U.S. PATENT DOCUMENTS

| | | | |
|---|---|---|---|
| 3,426,749 | 2/1969 | Jephcott | 128/11 |
| 3,762,400 | 10/1973 | McDonald | 128/18 |
| 3,851,642 | 12/1974 | McDonald | 128/18 |
| 4,492,220 | 1/1985 | Hayes | 128/17 |
| 4,579,108 | 4/1986 | Baaman | 128/10 |
| 4,597,382 | 7/1986 | Perez | 128/17 |
| 4,643,172 | 2/1987 | Taff et al. | 128/16 |

FOREIGN PATENT DOCUMENTS 506409  5/1976  U.S.S.R. ................................. 128/3

Primary Examiner—Richard C. Pinkham
Assistant Examiner—Mark S. Graham
Attorney, Agent, or Firm—Krass & Young

[57] ABSTRACT

A disposable cover of a novel type is provided for each of the blades of a vaginal speculum to prevent cross contamination of patients examined by the same instrument but also to allow for improved surgical visibility.

1 Claim, 1 Drawing Sheet

SPECULUM PROTECTOR

DESCRIPTION

1. Technical Field

This invention relates to surgical instruments and, more particularly, to techniques for preventing cross contamination of a patient examined by means of a vaginal speculum.

2. Background Art

A vaginal speculum is an important medical instrument which serves as an expedient means for providing examination and treatment of the vagina and related areas. Examples of this relatively old instrument are found in U.S. Pat. Nos. 662,830 and 2,672,859.

A vaginal speculum comprises, briefly, a composite frame assembly having a pair of protruding blades which are inserted into the vagina and thereafter separated or opened to provide a channel for visual examination and treatment. Medical practitioners require a vaginal speculum which lends itself to manual dexterity. The design of the conventional vaginal speculum enables the blades to be sufficiently movable to provide not only parallel but angularly displaced adjustment of the blades over a wide range of separation.

The most commonly used vaginal specula are made of metal such as stainless steel and are designed to have long, useful lives. However, after each use the instrument must be cleaned and sterilized as a medical necessity to prevent transfer of harmful bacteria or other contamination from one patient to another. Such cleaning practices are time consuming as well as undesirable and menial tasks. At the same time these practices tend to limit the number of vaginal examinations which may be accomplished in a given time period unless a large number of these instruments are available. The number of vaginal examinations being performed has drastically increased in all areas of medical diagnosis and treatment. As a consequence, significant quantities of these relatively expensive instruments must be procured thereby requiring a sizable investment even for the single practitioner.

Even if many instruments are available to the practitioner it is still difficult to insure absolute sterility using conventional methods of cleaning the vaginal speculum. The medical literature has reported several strains of bacterial spores which are particularly adapted for prolonged survival under adverse conditions. These strains are relatively resistant to killing by heat, as well as by drying, freezing, toxic chemicals and radiation. In fact, some of the most heat-resistant spores have been known to survive boiling for many hours. See, e.g., Davis et al, *Microbiology*, 34d Edition, pages 102, 108; Freeman, *Textbook of Microbiology*, pages 122-131, and 819; and Jokik et al, *Zinsser Microbiology*, 17th Edition, pages 281-282, 292-294, 1341-1440. Hence, the possibility of cross contamination remains a very real possibility.

In an effort to prevent this cross contamination problem the art has almost exclusively directed its efforts towards providing disposable specula which may be thrown away after the examination of one patient. Representative examples of disposable vaginal specula disclosed in the patent literature are found in U.S. Pat. Nos. 3,815,585; 3,890,961; and 4,263,898. In general, these disposable instruments are made of plastic which by their nature are more resilient than the conventional permanent metallic speculums. Unfortunately, many of the disposable specula are comparatively difficult to manipulate, do not provide a wide range of adjustment, or are much more expensive to use in the long run when compared to the permanent type of vaginal speculum.

Recently, the problem of preventing cross contamination has been overcome through the use of a vaginal speculum single-use protector or disposable cover for each of the blades of the instrument, as described in my U.S. Pat. No. 4,492,220. Use of a disposable cover of this single blade type, formed of oblong sheets of plastic film fused together, is practical and economical. However, it is found that in use the sheet material tends at times to hang down and to lose its shape and being bag-like is difficult to orient. Also it is possible to put the known cover on in an inverted fashion with the toe extending on the inner surface rather than the outer surface. Further, the known cover provides little if any cushion against the metal blades of the speculum. Also, in the space close to the convex surfaces of the blades the compliance of the cover can undesirably be imperfect especially in the zone below the concave undersurface of the upper blade, so that the concavity of the viewing channel between the spaced blades is diminished and the field of vision thus is impaired so that a need exists for means of realizing all of the benefits of compliance and full vision without sacrificing or compromising the advantages of the disposable speculum cover concept.

SUMMARY OF THE INVENTION

It is the primary object of this invention to provide a technique for using disposable covers for the blades of permanent type vaginal specula and obtaining all of their recognized advantages while at the same time improving their handling characteristics and properties in an economical and practical manner.

Pursuant to the present invention, a disposable speculum blade cover of a novel type is provided. The blade cover is to be used, as one of a pair of disposable covers, with a vaginal speculum including a lower blade and an upper blade with opposing concavo-convex blade surfaces that can be separated or opened to provide a concave walled viewing and access channel therebetween for visual examination and treatment of a patient, the cover having a flexible elastic sleeve-like body, preferably transparent, having an outwardly flared open end and being adapted to be placed in covering protective relation over a speculum blade. The cover body is formed of a suitable material such as a resilient polymeric resin or plastic material which is capable of undergoing a temporary memory shift, the outwardly flared open end being structured such that said end of the blade cover can be partly opened with two hands and when partly open for purposes of insertion of the blade can be fully opened with one hand by inward radial compression of its opposite side edges at the open end such that said cover undergoes a temporary memory shift and temporarily remains fully opened upon release of the compression to a relaxed state thereby facilitating insertion of the speculum blade into the blade cover. The cover in a relaxed state has a dimensionally stable concavo-convex shape and size closely resembling a speculum blade but slightly larger so that when a pair of covers is placed in covering relation over the respective speculum blades each of the covers is substantially unstressed and retains its concavo-convex shape intimately matching the respective concave blade surface without voids therebetween thus maximizing the magnitude of the concavity of said viewing channel for purposes of enhanced surgical accessability and visibility. The cover is adapted to surround and closely conform to substantially the entire length and sides of the blades of the speculum. The cover is made of a suitable material that prevents bi-directional transfer of harmful bacteria or other organisms from the blade to the patient or vice versa. In a preferred embodiment, the cover is made by molding, using a medical grade flexible polymeric resin or plastic molding material formed on a speculum blade or smooth metal mold form having the shape of a speculum blade. Conveniently, the blade form is first coated with a silicone release agent to prevent adhesion of the molding material to the form and then further coated by dipping into a liquid resin solution, dried and the dried coating cut to length and stripped from the mold. The coating of the liquid resin on the mold is made sufficiently thick to result in the finished molded blade cover having 3-dimensional stability in the relaxed state but also being readily flexible and manipulatable. A preferred wall thickness is about 20 to about 35 mils. The finished blade cover is sterilized by suitable means, such as autoclaving or treatment with ethylene oxide gas, and sterile packaged. Preferred molding materials are vinyl homopolymers and copolymers, especially polyvinylchloride (PVC, *Modern Plastics Encyclopedia*, 1983–1984, page 84 et seq., McGraw-Hill). The smooth surface of the plastic facilitates slipping the cover onto the speculum blade and insertion of the instrument into the patient. In the disclosed embodiment, the cover is formed with a nonoverlapping portion on the rear or open end to aid in opening and pulling the cover onto the blade.

According to the method of this invention a disposable cover is slipped onto each of the blades prior to examining the patient. After the examination the covers are removed and disposed. The new covers are slipped onto the speculum blades prior to examining the next patient.

Among the advantages of the present invention is that the same permanent type of vaginal speculum may be used for examining several patients while minimizing the chances of cross contamination. None of the manipulative features are impaired by use of the bacteria-impervious covers. As a result, there are few disadvantages of using the concept of this invention and a host of advantages that can be achieved in a simple, low cost manner.

BRIEF DESCRIPTION OF THE DRAWINGS

These and other objects and advantages of the present invention will become apparent to one skilled in the art upon reading the following specification and by reference to the drawings in which.

DESCRIPTION OF THE PREFERRED EMBODIMENT

Figure 1:
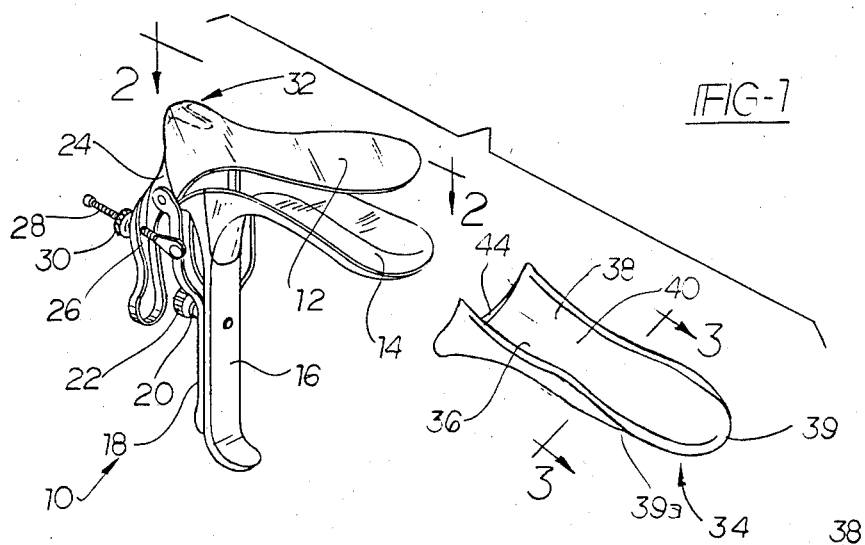
FIG. 1 is an exploded perspective view showing one cover of the preferred embodiment on the top blade of a vaginal speculum and the cover for the lower blade displaced therefrom.
Figure 4:
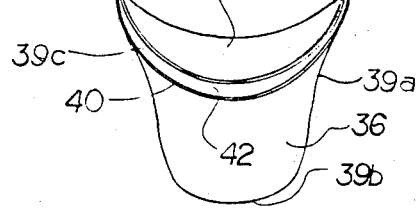
FIG. 4 is a view of the open end of a preferred embodiment of a speculum blade cover, in perspective.

Referring now to the drawings, a conventional vaginal speculum made of stainless steel or the like and adapted for a permanent use is designated by the reference numeral 10. Speculum 10 includes a pair of spreadable or dilatable blades 12 and 14 which are pivotally and slidably coupled together for movement toward and away from each other. A handle 16 is formed integrally with blade 14. A blade positioning slide 18 is mounted on the handle 16 by a threaded bolt 20 which extends through a slot in the slide. A knurled nut 22 is threaded onto bolt 20 and serves to lock the handle 16 and slide 18 together. When the nut 22 is loosened, the slide 18 can be translated along the handle 16 between the extreme positions defined by the ends of the slot.

A depending adjustment arm 24 is formed integrally with the rearward portion of the top blade 12. A rivet 26 extends through aligned apertures in the slide 18 and arm 24 to pivotally mount the blade 12. An adjusting screw 28 connects one end region of arm 24 with the slide 18. A knurled nut 30 is threaded onto adjusting screw 28 and serves to retain the blade 12 at a selected position relative to the lower blade 14.

The construction of speculum 10 as thus far described is old in the surgical art. Speculum 10 is intended for repeated use and is commonly made of stainless steel or other metals which will withstand repeated sterilization. Hereinafter, these conventional specula shall be referred to as permanent specula. In use, permanent specula are manipulated so as to close the blades 12,14 for insertion into the patient and then adjusted to space the blades to provide a viewing area for the physician.

Figure 2:
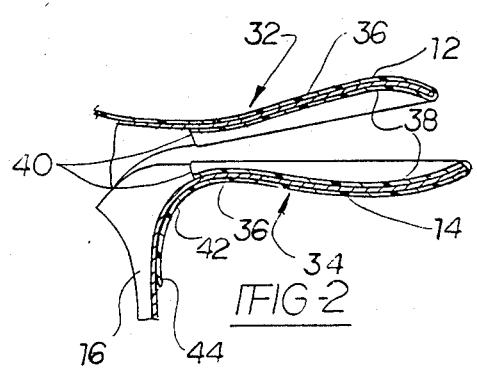
FIG. 2 is a fragmentary side cross-sectional view along the lines 2—2 of FIG. 1 showing both covers in place.
Figure 5:
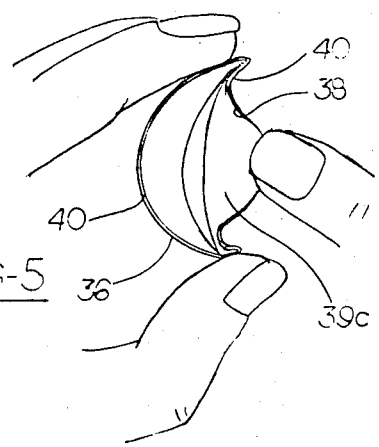
FIG. 5 is a view similar to that of FIG. 4 showing a preferred feature in the manner of opening a speculum cover according to the invention.
Figure 3A:
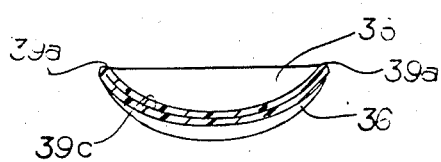
FIG. 3a is a cross-sectional view along the lines 3—3 of FIG. 1.
Figure 3B:
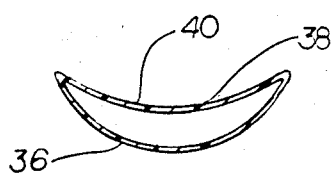
FIG. 3b is a similar view of the prior art cover, for comparison.
Figure 6:
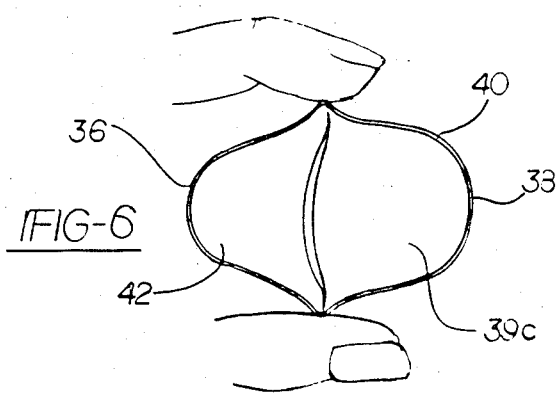
FIG. 6 is a similar view illustrating the structural feature of the cover whereby, as it is found, slight inward radial compression on the side edges of the cover after opening with two hands as in FIG. 5 causes the cover opening to become greatly enlarged and dimensionally stable in the open position, as shown, thereby freeing one hand or both hands if desired and so facilitating the step of slipping the opened cover onto the speculum blade.

Pursuant to the present invention a pair of sterile covers 32,34 are provided for covering those portions of the blades 12,14, respectively, that are designed to come into contact with the patient during examination. Each of the covers 32,34 are identical and, thus, a description of the construction for one of them will suffice for both. The covers each take the form, in the preferred embodiment, of a flexible elastic sleeve-like body formed as by molding in a single piece of polymeric plastic or resin material having a convex wall 36, a concave wall 38, a side edge 39a, a closed end 39b, and an outwardly flared open end with an opening 39c defined by a rearward edge 40. The overlapping portions of sheets 36 and 38 extend substantially the entire length of its respective blade as shown most clearly in FIG. 2. As shown therein, the covers are dimensioned so that they closely conform to both the upper and lower portions of their respective blades.

The rearward edge 40 of the cover walls 36,38 defines an elongated opening 39c so that the covers may be slipped onto the blades. In the preferred embodiment, the nonoverlapped portion 42 of the wall 34 is of sufficient length so that it may serve to protect the forward upper portion of the speculum handle 16 from coming into contact with the outer tissues of the patient. The rear extremity of the wall 36 may include a tab portion (not shown) which may be grasped by the user to aid in slipping the cover onto the blade without touching the cover portions that may come into contact with the patient.

In the particular example disclosed herein, covers 32,34 are made of medical grade plastic resin such as polyvinyl chloride resin that in molded form is soft and warm to the touch, resilient, and provides a forgiving cushion in contrast to the hard steel blade surfaces of the speculum. The covers advantageously have a memory or regain and are compressible and flexible so that when released from a distorted or compressed state, they regain their original geometry in a relaxed state.

In use, the covers 32 and 34 are grasped by their respective nonoverlapped portions and slipped onto the distal end of blades 12 and 14, respectively. Note that the smooth surface provided by the covers reduces friction and enables the covers to be positioned on the blades easily. Note also that while the covers 32 and 34 are identical, the lower cover 34 is rotated 180° about its longitudinal axis for use with the lower blade 14. In such manner, not only is the blade 14 covered but the nonoverlapping rearward portion 42 of the cover is brought into position in front of the upper portions of the handle 16. The covered speculum blades are then inserted into the patient and the speculum 10 is adjusted to dilate the vagina by adjusting the position of the blades using the same techniques as the physician normally uses with the conventional speculum 10. Because the covers 34,36 closely conform to the blades, the physican's view is not obstructed. Since separate covers are provided for each of the blades the side walls of the vaginal area are not obstructed from view and may be accessed for treatment. The wall thickness of the cover (preferably uniform throughout in each instance) is sufficient to provide an insulative cushion against traumatic exposure preferably being at least about 20 mils to about 35 mils in thickness. Thus the covers are thicker than conventional covers (e.g. 20 mils vs. 5 mils) an added benefit being found that the relatively thick cover is practically impossible to become inverted of otherwise disoriented. The smooth surfaces of the covers also facilitate easy insertion of the instrument and minimize abrasion. Since lubricants for the blades cannot generally be used, the covers thus provide an added benefit in that they minimize the discomfort often experienced by the patient when conventional uncovered speculums are used. The covers also give the feeling of warmth not normally experienced with bare metal coming into contact with the patient.

One of the most important advantages of the present invention is that the covers prevent the transfer of harmful bacteria, viruses or other organisms from the blades to the patient or vice versa. The covers isolate not only the outer surfaces of the blades from the patient but also the substantial entirety of the inner portion of the blades as well. Consequently, the chances of cross contamination of patients being examined by the same instrument is substantially minimized.

After the examination is completed, the blades are adjusted so that they become closely spaced and the instrument is removed from the patient. Note that the design of the covers still permit the practitioner to obtain access to all of the adjustment devices of the conventional speculum. After the instrument has been removed, the covers are grasped by the open end portions (which generally do not come into contact with patient) and the covers are slipped off of the blades and thrown away. New covers are then slipped over the blades of the speculum for examining the next patient.

It is believed that the covers of the present invention will eliminate the need for scrubbing and autoclave sterilization of the instrument between uses. A simple wash in cold sterilization solution and drying in air may be all that is necessary. The use of the covers also has the added benefit of minimizing the possibility of infecting the nurses or physicians that clean the instrument. Finally, it should be understood that while this invention has been described in connection with a particular example thereof, other modifications and advantages of the invention will become apparent to one skilled in the art after the study of the specification, drawings and following claims.

I claim:

1. A blade cover to be used as one of a pair of disposable covers with a speculum of the type including a lower blade and an upper blade with opposing concavo-convex blade surfaces that can be separated or opened to provide a concave walled viewing channel therebetween for visual examination and treatment of a patient, each cover having opposite sides edges and a flexible elastic hollow or sleeve-like body having an outwardly flared open end adapted to be placed in covering protective relation over a specimen blade, the body being formed of a polymeric resin or plastic material which is capable of undergoing a temporary memory shift, the outwardly flared open end being structured such that said end of the blade cover can be partly opened with two hands and when partly open for purposes of insertion of the blade can be fully opened with one hand by inward radial compression of its opposite side edges at the open end such that said cover undergoes a temporary memory shift and temporarily remains fully opened upon release of the compression to a relaxed state thereby facilitating insertion of the speculum blade into the blade cover, the body further having in a relaxed state a dimensionally stable concavo-convex shape and size closely resembling but slightly larger than a speculum blade, so that when a pair of said covers is slipped in covering relation over and in contact with the respective speculum blades, each of the covers is substantially unstressed and retains its concavo-convex shape intimately matching, surrounding and closely conforming to substantially the entire length and sides of the respective blade surfaces without extensive voids therebetween, thereby maximizing the magnitude of the concavity of said viewing channel for purposes of enhanced surgical visibility.

* * * * *

UNITED STATES PATENT AND TRADEMARK OFFICE
CERTIFICATE OF CORRECTION

PATENT NO. : 4,807,600

DATED : February 28, 1989

INVENTOR(S) : Hayes

It is certified that error appears in the above-identified patent and that said Letters Patent is hereby corrected as shown below:

Column 1, line 51, "most" should be --more--.

Column 3, line 33, "on the rear" should be --on a rear--.

Column 3, line 38, "The" should be --Then--.

Column 6, line 34, "sides" should be --side--.

Column 6, line 37, "specimen" should be --speculum--.

Signed and Sealed this

Twenty-first Day of November, 1989

*Attest:*

JEFFREY M. SAMUELS

*Attesting Officer*     *Acting Commissioner of Patents and Trademarks*